(12) United States Patent
Lecomte et al.

(10) Patent No.: US 8,535,390 B1
(45) Date of Patent: Sep. 17, 2013

(54) TRACTION DEVICE AND ASSOCIATED ATTACHMENT DEVICE FOR A PROSTHETIC RUNNING FOOT

(75) Inventors: Christophe Lecomte, Reykjavik (IS); Sindri P. Sigurdsson, Reykjavik (IS); Larus Gunnsteinsson, Reykjavik (IS); Michael R. Friton, Portland, OR (US); Tobie D. Hatfield, Lake Oswego, OR (US)

(73) Assignee: Össur hf, Reykjavik (IS)

( * ) Notice: Subject to any disclaimer, the term of this patent is extended or adjusted under 35 U.S.C. 154(b) by 69 days.

(21) Appl. No.: 13/235,324

(22) Filed: Sep. 16, 2011

(51) Int. Cl.
*A61F 2/68* (2006.01)
(52) U.S. Cl.
USPC .......................................................... 623/53
(58) Field of Classification Search
USPC .................................................... 623/53–56
See application file for complete search history.

(56) References Cited

U.S. PATENT DOCUMENTS

| 4,267,650 | A | 5/1981 | Bauer |
| 5,593,453 | A | 1/1997 | Ahlert et al. |
| 5,593,456 | A | 1/1997 | Merlette |
| 6,165,228 | A | 12/2000 | Lindh |
| 6,311,415 | B1 | 11/2001 | Lind |
| 6,596,029 | B1 | 7/2003 | Gramnas |
| 6,811,571 | B1 | 11/2004 | Phillips |
| 7,954,502 | B2 | 6/2011 | Townsend et al. |
| 2006/0015192 | A1 | 1/2006 | Clausen et al. |
| 2006/0069450 | A1* | 3/2006 | McCarvill et al. ............. 623/55 |
| 2006/0185703 | A1 | 8/2006 | Townsend et al. |
| 2009/0299490 | A1 | 12/2009 | Summit |
| 2012/0271434 | A1* | 10/2012 | Friesen et al. .................. 623/55 |

OTHER PUBLICATIONS

Otto Bock C-Sprint® product, Otto Bock Prosthetics—Lower Extremities Catalog, p. 102, 2009.

\* cited by examiner

*Primary Examiner* — Bruce E Snow
(74) *Attorney, Agent, or Firm* — Knobbe, Martens, Olson & Bear, LLP

(57) ABSTRACT

A traction device for a prosthetic running foot having a curved profile and mechanisms for attaching the traction device to the prosthetic running foot are provided. The traction device includes a sole portion for traction and a midsole for improved rollover. The traction device has fasteners (e.g., clamps) that attach to the top of the prosthetic running foot or a cavity that removably receives the toe of the prosthetic running foot. The traction device also has a strap that removably couples to a clip permanently or removably attached to the top surface of the prosthetic running foot.

12 Claims, 5 Drawing Sheets

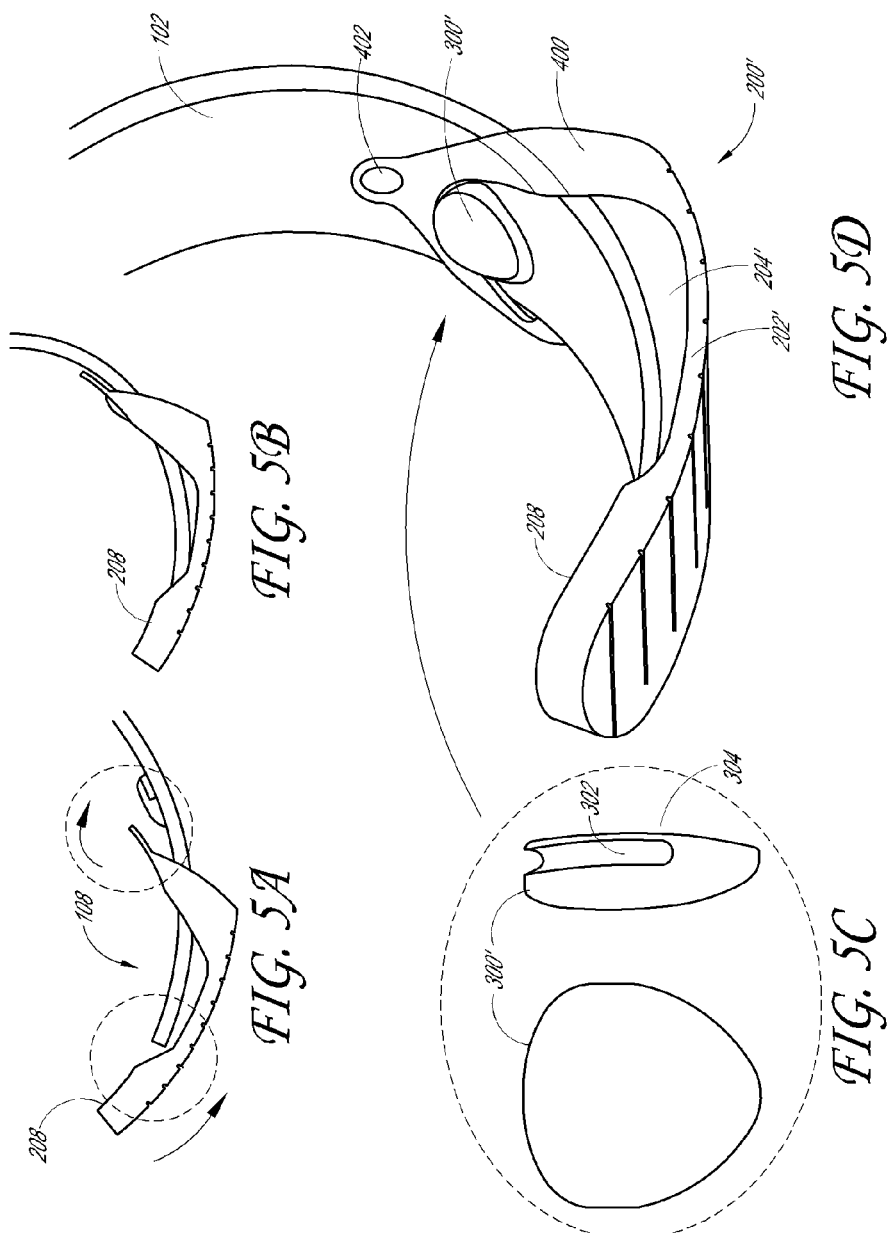

TRACTION DEVICE AND ASSOCIATED ATTACHMENT DEVICE FOR A PROSTHETIC RUNNING FOOT

CROSS-REFERENCE TO RELATED APPLICATIONS

This application is related to co-pending application Ser. No. 29/401,927 filed Sep. 16, 2011, titled TRACTION DEVICE FOR A PROSTHETIC RUNNING FOOT, the entire contents of which is hereby expressly incorporated by reference and should be considered a part of this specification.

BACKGROUND

1. Field

The present application relates to foot prostheses in general, and more particularly, to a traction device configured to removably attach to a prosthetic running foot with a curved profile.

2. Description of the Related Art

Various types of prosthetic foot devices are available as substitutes for human feet. Some prosthetic feet are designed especially for sporting activities such as running, both at the recreational and competitive levels. Examples of prosthetic running feet commercially available are the Össur® Flex-Run™, Össur® Flex-Sprint™, and Össur® Cheetah®. Prosthetic running feet are typically designed to efficiently store and release energy produced during running to improve performance. Such feet can have a traction sole surface (e.g., running spikes) that are adhered or bonded to the bottom of the prosthetic foot. However, there is a need for a sole designed to be removably attached to the bottom of a prosthetic running foot and that can advantageously enhance traction on a running surface, improve foot rollover and performance, and protect the prosthetic running foot from wear.

SUMMARY

In some embodiments, a traction device for a prosthetic running foot includes a sole portion, a midsole, a clip, and a strap. The midsole is attached to the sole portion and disposed between the sole portion and a bottom surface of a prosthetic running foot when the traction device is attached to the foot. The clip is configured to be attached to a top surface of the prosthetic running foot. The strap is attached to the sole portion and configured to removably couple to the clip to secure the traction device to the prosthetic running foot.

In some embodiments, a prosthetic running foot includes a plate-like foot element having a distal portion with a curved profile and a traction device. The traction device is configured to removably attach to the distal portion of the foot element on the plantar surface.

For purposes of summarizing the disclosure and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 5A illustrates a side view of another embodiment of a traction device as it is being attached to a prosthetic running foot.

FIG. 5B illustrates a side view of the traction device and prosthetic running foot of FIG. 5A after the combination is assembled.

FIG. 5C illustrates front and side views of one embodiment of a clip.

FIG. 5D illustrates a perspective view of the assembled prosthetic running foot and traction device of FIG. 5B.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Figure 1:
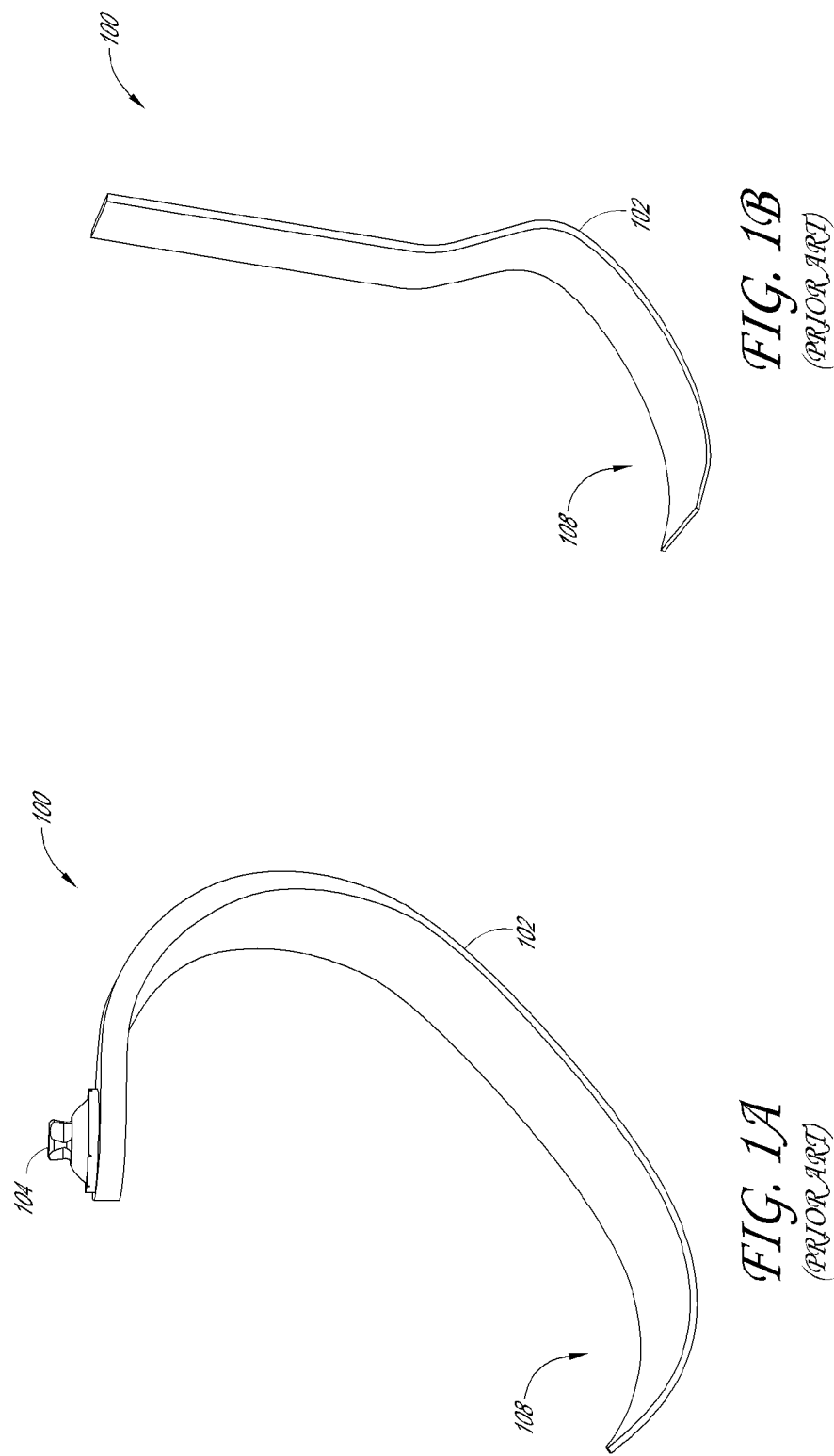
FIG. 1A illustrates a perspective view of one embodiment of a prosthetic running foot.
FIG. 1B illustrates a perspective view of another embodiment of a prosthetic running foot.

FIGS. 1A and 1B illustrate example embodiments of a prosthetic running foot 100. Prosthetic running feet such as those illustrated in FIGS. 1A and 1B are designed to efficiently store and release energy produced during running to improve performance. The prosthetic running foot 100 has a plate-like member 102. In some embodiments, such as the embodiment shown in FIG. 1A, the plate-like member 102 has an overall curved profile. In other embodiments, such as the embodiment shown in FIG. 1B, the plate-like member 102 has a "J" shape comprising a substantially straight and vertical proximal portion and a generally curved distal portion. A proximal portion of the plate-like member can have an attachment adapter 104 for connecting the prosthetic foot to a user's residual limb or to another prosthetic component (e.g., pylon, socket). The example prosthetic running feet shown in FIGS. 1A and 1B are the Össur® Flex-Run™ and Össur® Cheetah®, respectively; however, it will be understood by one of skill in the art that the devices described herein can also be adapted for use with other prosthetic running feet, and such variations are considered within the scope of the present disclosure. The prosthetic running feet in FIGS. 1A-1B have a monolithic member 102 made of carbon fiber. However, in other embodiments, the prosthetic running foot can be modular and made of other suitable materials.

Figure 2:
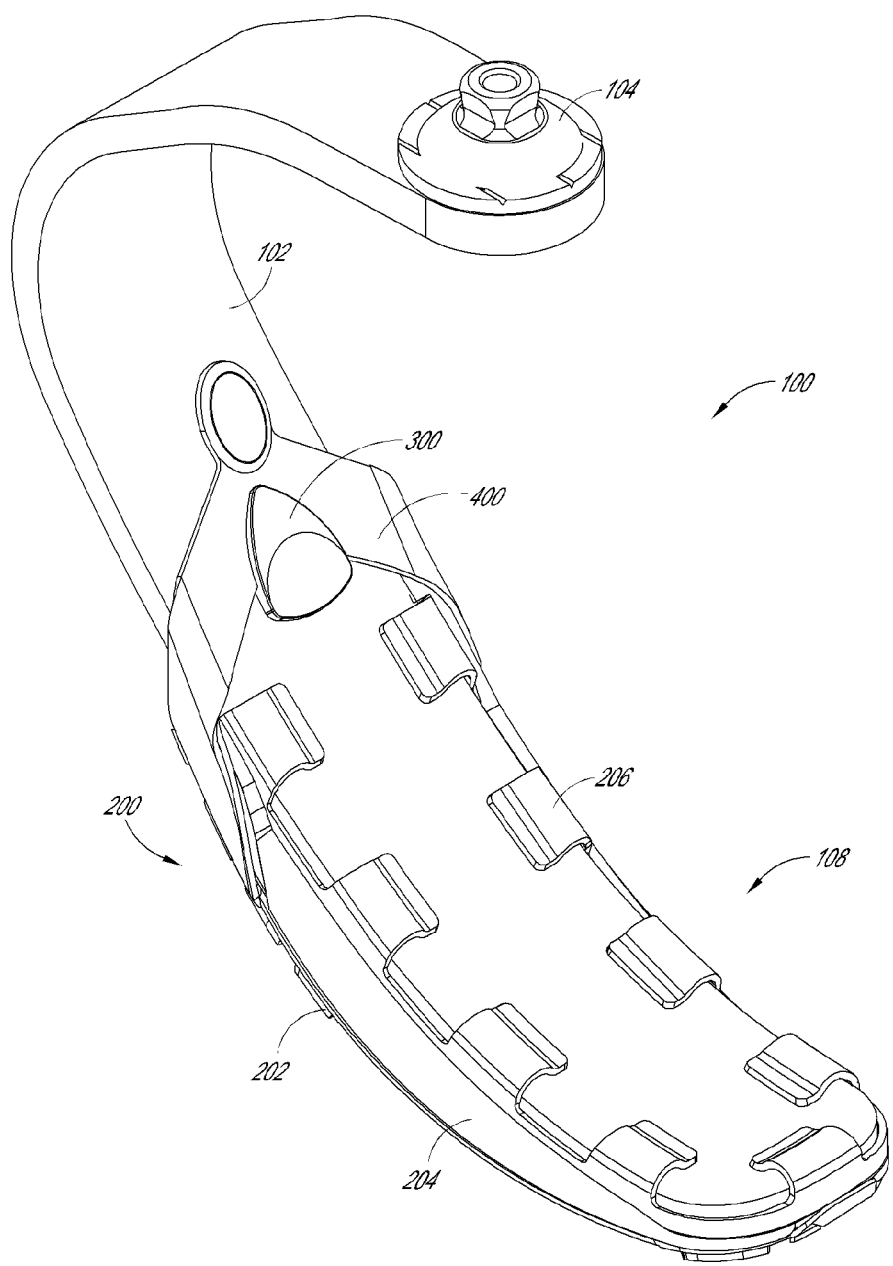
FIG. 2 illustrates a perspective view of one embodiment of a traction device attached to the prosthetic running foot of FIG. 1A.
Figure 3:
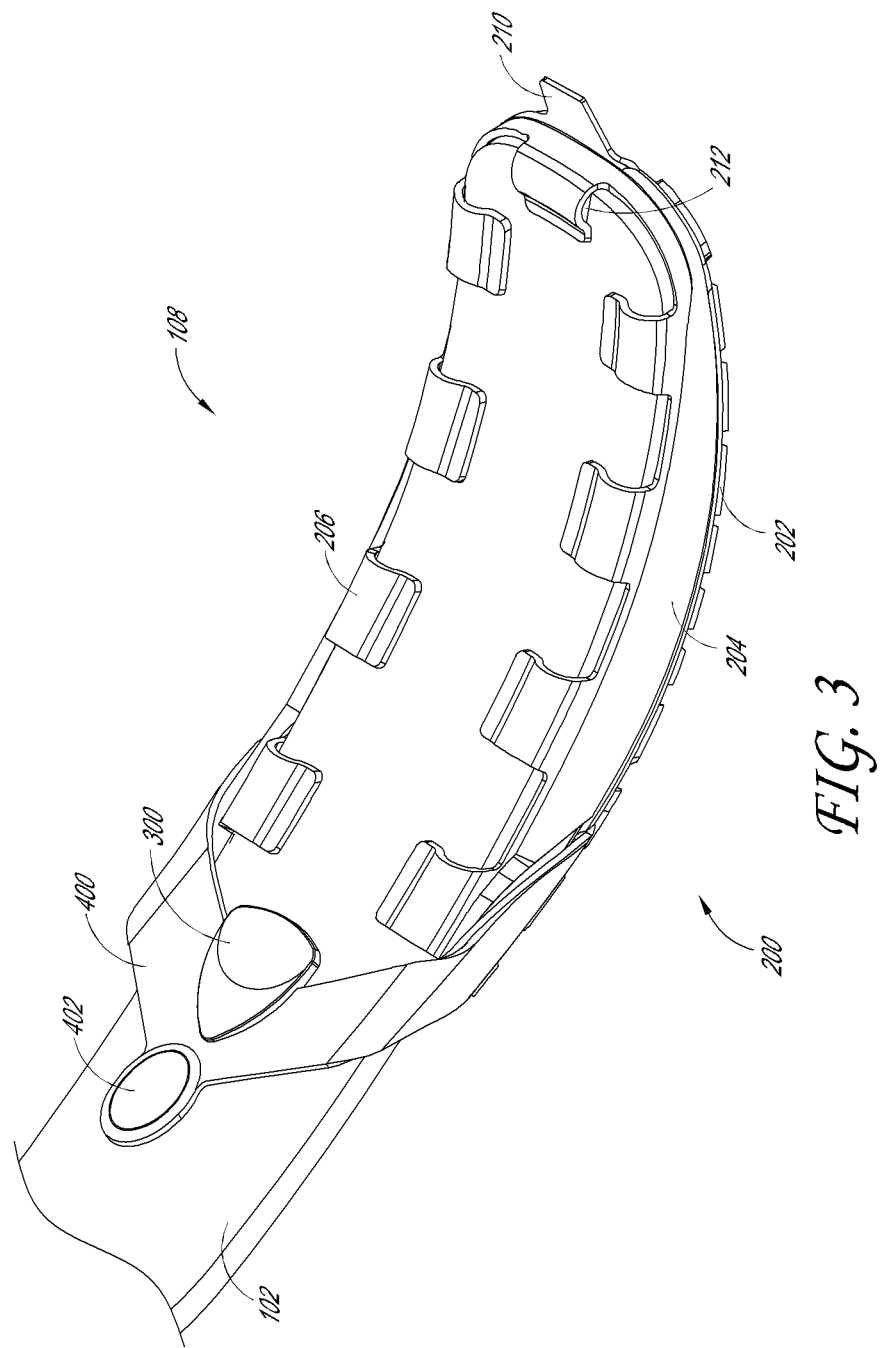
FIG. 3 illustrates a perspective view of the distal end of a prosthetic running foot with the traction device attached to the prosthetic running foot.
Figure 4:
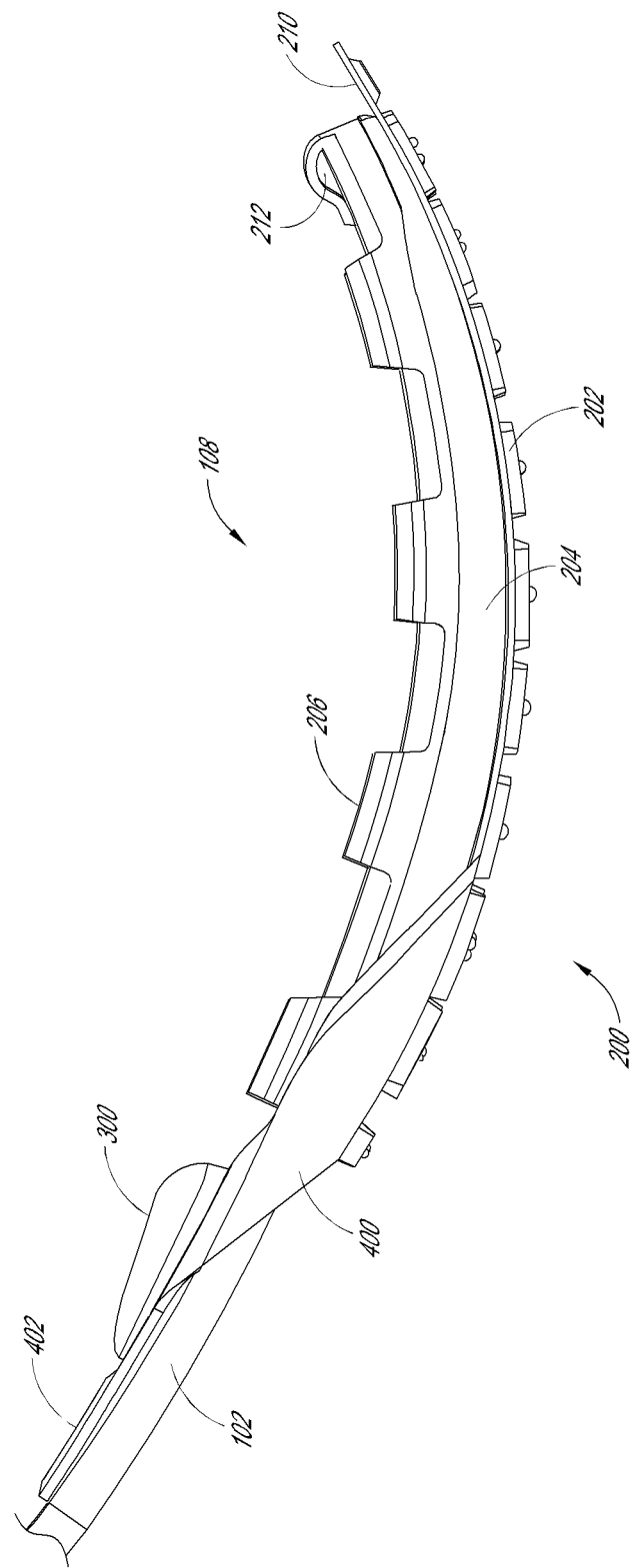
FIG. 4 illustrates a side view of the distal end of a prosthetic running foot with the traction device attached to the prosthetic running foot.

FIGS. 2-4 illustrate an embodiment of a traction device 200 attached to a prosthetic running foot 100 such as the prosthetic running foot 100 shown in FIG. 1A. The traction device 200 is configured to removably attach to the bottom of the distal portion 108 of the prosthetic running foot 100. The traction device 200 can have a sole portion 202 and a midsole 204, where the midsole 204 is disposed between the sole portion 202 and the bottom surface of the prosthetic running foot 100 when the traction device 200 is attached to the prosthetic foot 100. The sole portion 202 can resemble and function similarly to a sole of an athletic shoe (e.g., have a treaded traction surface). The sole portion 202 advantageously provides traction with a running surface, absorbs impact, and helps protect the prosthetic foot 100 from wear. The midsole 204 is designed to be disposed between the prosthetic foot 100 and the sole portion 202 to provide improved shock absorption and foot rollover during use. The sole portion 202 can be made of, for example, rubber, and the midsole 204 can be made of, for example, ethylene vinyl acetate (EVA). Other resilient materials are also possible. In some embodiments, the sole portion 202 and midsole 204 are integrally formed or permanently adhered together. Alternatively, in other embodiments, the sole portion 202 is removably attachable to the midsole 204.

In one embodiment, the midsole 204 can have the same stiffness along the length of the traction device 200. In another embodiment, the midsole 204 and/or sole portion 202 can have different sections of differing stiffness, such that the traction device 200 guides the rollover of the prosthetic running foot 100 in a desired direction. The sections of different stiffness can be separate inserts attachable to the sole portion 202 and/or midsole 204, or sections embedded in the midsole 204 and/or sole portion 202 during manufacture of the traction device 200 so that the sections of different stiffness are monolithic (i.e., one piece) with the rest of the midsole 204 or sole portion 202. In one embodiment, the midsole 204 and/or sole portion 202 can have a different stiffness on a medial side thereof than a stiffness on a lateral side thereof. For example, the midsole 204 and/or sole portion 202 can have a lower relative stiffness on the medial side and a higher relative stiffness on the lateral side, so that the traction device 200 guides rollover of the prosthetic running foot 100 toward the medial side during running. Further information on varying stiffness to guide foot rollover can be found in U.S. Pat. No. 7,347,877, filed Sep. 17, 2004, titled "Foot Prosthesis with Resilient Multi-Axial Ankle" and US Publication No. 2006/0015192, filed May 26, 2005, titled "Functional Foot Cover," the entire contents of both of which are hereby incorporated by reference and should be considered a part of this specification.

With reference to FIGS. 2 and 4, the midsole 204 can have a thickness that decreases from a posterior portion of the traction device to an anterior portion of the traction device, so as to guide rollover forwardly. In another embodiment, the midsole 204 can have a uniform thickness along the length of the traction device 200. In still another embodiment, the thickness of the midsole 204 can vary between the medial and lateral sides of the traction device 200 (e.g., be thicker on the lateral side relative to the medial side) to provide a desired rollover effect. In one embodiment, the width of the sole portion 202 can be generally equal to the width of the prosthetic foot 100. In another embodiment, the width of the sole portion 202 can be greater than the width of the prosthetic foot 100 along at least a portion of the length of the traction device 200, so as to provide increased stability during running.

FIGS. 2-4 show an example embodiment of a mechanism for attaching the traction device 200 to the prosthetic running foot 100. In the illustrated embodiment, the traction device 200 can have one or more fasteners, such as clamps, 206 that extend over an edge (e.g., side edge, distal edge) of the foot 100 and attach to the top of the prosthetic foot 100. In the illustrated embodiment, the traction device 200 can have four clamps 206 on each side and one clamp 206 on the distal end or toe as shown in FIGS. 2-4, but other numbers and arrangements of clamps 206 are also possible. The clamps 206 can be made of, for example, a plastic material. Other materials are also possible. In other embodiments, the traction device 200 can have other suitable fasteners (e.g., screws, detents, press-fit, slots). In some embodiments, the sole portion 202 of the traction device 200 can include a tab 210 that can be folded upward and adhered to the distal edge of the traction device 200 or to a fastener 206 on the distal edge of the traction device 200 to form a front bumper.

In use, a user slides the traction device 200 proximally onto the prosthetic foot 100 from the distal end of the prosthetic foot 100 such that the distal portion 108 of the plate-like member 102 slides between the clamps 206 and the top surface of the traction device 200. In some embodiments, the distal end of the plate-like member 102 has a protrusion 212. A clamp 206 on the distal end or toe of the traction device 200 can lock onto the protrusion 212. The plate-like member 102 can include additional protrusions 212 corresponding to other clamps 206 on the traction device 200.

FIGS. 5A, 5B, and 5D show another embodiment of a traction device 200' that removably attaches to the prosthetic running foot 100. The traction device 200' is similar to the traction device 200, except as noted below. Thus, the reference numerals used to designate the various components of the traction device 200' are identical to those used for identifying the corresponding components of the traction device 200 in FIGS. 2-4, except that a "'" has been added to the reference numerals. In the illustrated embodiment, the front or toe portion 208 of the traction device 200' can include a cavity or slot configured to removably receive the toe or distal portion 108 of the prosthetic running foot 100. The toe portion 208 of the traction device 200' loops over or wraps around at least a portion of the toe or distal portion 108 of the prosthetic running foot 100 and functions as a fastener to fasten the traction device 200' to the prosthetic running foot 100.

As shown in FIGS. 2-5D, the traction device 200, 200' can also have a strap 400 configured to be attached to a clip 300, 300' on the prosthetic foot 100. The clip 300, 300' and strap 400 are configured to be removably coupled to each other to help secure the traction device 200, 200' to the prosthetic running foot 100.

The clip 300, 300' can be permanently or removably attached to the top surface of the prosthetic running foot 100. In the illustrated embodiment, the clip 300, 300' can be generally shaped as an acute isosceles triangle. The apex of a triangle-shaped clip 300, 300' can be oriented toward the proximal end of the prosthetic foot as shown in FIGS. 2-4 or toward the distal end of the prosthetic foot as shown in FIG. 5D. Other clip 300, 300' shapes are also possible. The clip 300, 300' can have a groove 302 that runs along the proximal edge of the clip 300, 300' and at least partially along both sides of the clip 300, 300'. The groove 302 can gradually increase in depth towards the proximal surface of the clip 300, 300'. The clip 300, 300' preferably has a slightly rounded back 304 that can follow or correspond to the contours of the curved plate-like member 102. The edges of the clip 300, 300' in contact with the plate-like member 102 can be steep to avoid peeling.

In one embodiment, the strap 400 can be integrally formed with the sole portion 202 of the traction device 200, 200'. Alternatively, the strap can be adhered or otherwise secured between the sole portion 202, 202' and the midsole 204, 204'. The strap 400 wraps over the top of the prosthetic running foot 100 to removably attach to the clip 300, 300'. The strap 400 can have a pull tab 402 that a user may grasp to attach and remove the strap 400 to and from the clip 300, 300'. In some embodiments, the pull tab 402 is ovular and can have a rubberized or textured surface to facilitate gripping by a user. The strap 400 can be made of an elastic material or a material having elastic properties, such as natural or synthetic rubber. However, other suitable materials can be used for the strap 400. In use, the user grasps the strap's pull tab 402 proximally to stretch the strap 400 over the top of the prosthetic running foot 100 and clip 300, 300' so that an edge of the strap 400 snaps into the groove 302 of the clip 300, 300'. To remove the traction device 200, the user again grasps the pull tab 402 and pulls the strap 400 proximally to release it from the groove 302 of the clip 300, 300'.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. A traction device for a prosthetic running foot, comprising:
   a sole portion;
   a midsole attached to said sole portion and configured to be disposed between said sole portion and a bottom surface of the prosthetic running foot when the traction device is attached to the prosthetic running foot;
   a clip configured to be attached to a top surface of the prosthetic running foot; and
   a strap attached to said sole portion;
      wherein said strap is configured to removably couple to said clip to secure the traction device to the prosthetic running foot,
      said strap further comprising a pull tab configured to be grasped by a user when attaching or detaching the traction device from the prosthetic running foot.

2. The traction device of claim 1 further comprising at least one clamp configured to contact a top surface of the prosthetic running foot and secure the traction device to the prosthetic running foot.

3. The traction device of claim 1, a toe portion of said sole portion further comprising a cavity configured to removably receive a toe portion of the prosthetic running foot.

4. The traction device of claim 1, wherein said pull tab comprises a textured surface.

5. The traction device of claim 1, wherein said strap comprises an elastic material.

6. The traction device of claim 1, wherein said sole portion comprises rubber.

7. The traction device of claim 1, wherein said midsole comprises ethylene-vinyl acetate.

8. A prosthetic running foot, comprising:
   a plate-like foot element having a distal portion with a curved profile;
   a clip configured to be attached to a top surface of the foot element; and
   a traction device configured to removably attach to the distal portion of the foot element on a plantar surface thereof, said traction device comprising a strap configured to removably couple to said clip, said strap comprising a pull tab configured to be grasped by a user to attach and detach said strap from said clip.

9. The prosthetic running foot of claim 8, said traction device comprising a sole portion and a midsole.

10. The prosthetic running foot of claim 8, said traction device comprising at least one clamp configured to contact said plate-like foot element to secure said traction device to said plate-like foot element.

11. The prosthetic running foot of claim 10, a top surface of said plate-like foot element comprising at least one protrusion, wherein said at least one clamp is configured to lock onto said at least one protrusion.

12. The prosthetic running foot of claim 8, said traction device comprising a cavity configured to removably receive a toe portion of said plate-like foot element.

\* \* \* \* \*